(12) United States Patent
Jahangir (10) Patent No.: US 11,298,525 B2
(45) Date of Patent: Apr. 12, 2022

(54) SYSTEMS AND METHODS FOR REDUCING LEAKS FROM A CATHETER

(71) Applicant: Abiomed, Inc., Danvers, MA (US)

(72) Inventor: Emilia Jahangir, Wenham, MA (US)

(73) Assignee: ABIOMED, INC., Danvers, MA (US)

( * ) Notice: Subject to any disclaimer, the term of this patent is extended or adjusted under 35 U.S.C. 154(b) by 388 days.

(21) Appl. No.: 16/515,480

(22) Filed: Jul. 18, 2019

(65) Prior Publication Data

US 2020/0023110 A1 Jan. 23, 2020

Related U.S. Application Data

(60) Provisional application No. 62/700,683, filed on Jul. 19, 2018.

(51) Int. Cl.

| | | |
|---|---|---|
| *A61M 60/50* | (2021.01) | |
| *A61M 60/148* | (2021.01) | |
| *A61M 60/205* | (2021.01) | |
| A61M 60/135 | (2021.01) | |
| A61M 60/857 | (2021.01) | |

(52) U.S. Cl.
CPC .......... *A61M 60/50* (2021.01); *A61M 60/148* (2021.01); *A61M 60/205* (2021.01); *A61M 60/135* (2021.01); *A61M 60/857* (2021.01)

(58) Field of Classification Search
CPC .. A61M 60/50; A61M 60/148; A61M 60/205; A61M 60/135; A61M 60/857
USPC .......................................................... 600/16
See application file for complete search history.

(56) References Cited

U.S. PATENT DOCUMENTS

| | | | |
|---|---|---|---|
| 5,921,913 A | 7/1999 | Siess | |
| 7,022,100 B1* | 4/2006 | Aboul-Hosn | A61M 60/422 604/6.11 |
| 2004/0052689 A1 | 3/2004 | Yao | |
| 2005/0267323 A1* | 12/2005 | Dorros | A61B 17/22 600/16 |
| 2005/0277803 A1 | 12/2005 | Pecor | |
| 2009/0093796 A1* | 4/2009 | Pfeffer | A61M 25/0074 604/530 |

(Continued)

OTHER PUBLICATIONS

International Search Report and Written Opinion Issued in PCT/US2019/042330 dated Oct. 21, 2019 (10 pages).

*Primary Examiner* — Aaron F Roane
(74) *Attorney, Agent, or Firm* — Botos Churchill IP Law LLP (57) ABSTRACT

Systems and methods are described herein relating to an intracardiac blood pump system comprising a pump, an elongate multi-lumen catheter, a compartment connected to the catheter, a first lumen, a conduit and a filter disposed within the conduit. At least one electronic element is located within the compartment. The conduit extends through an interface between the compartment and the catheter. The conduit is configured to allow gas to penetrate from a first end of the conduit through the first opening of the compartment to a second end of the conduit. The second end of the conduit is in fluid communication with a central lumen of the elongate multi-lumen catheter. The filter is configured to prevent egress of liquid from the multi-lumen catheter into the compartment after allowing flow of gas from the first end of the conduit through the second end of the conduit and into the multi-lumen catheter.

20 Claims, 6 Drawing Sheets

(56) References Cited

U.S. PATENT DOCUMENTS

| | | | | |
|---|---|---|---|---|
| 2011/0282274 A1* | 11/2011 | Fulton, III | ........ | A61M 25/1018 |
| | | | | 604/28 |
| 2014/0275725 A1* | 9/2014 | Schenck | ............. | A61M 60/148 |
| | | | | 600/16 |
| 2015/0290372 A1* | 10/2015 | Muller | ................ | A61M 60/857 |
| | | | | 600/424 |
| 2015/0374213 A1* | 12/2015 | Maurice, Jr. | ........... | A61B 1/015 |
| | | | | 600/157 |

* cited by examiner

SYSTEMS AND METHODS FOR REDUCING LEAKS FROM A CATHETER

REFERENCE TO RELATED APPLICATIONS

This application claims priority to and the benefit of U.S. Provisional Patent Application No. 62/700,683, filed on Jul. 19, 2018, and entitled "SYSTEMS AND METHODS FOR REDUCING LEAKS FROM A CATHETER". The entire contents of the above-referenced applications are incorporated herein by reference.

BACKGROUND

Intracardiac heart pump assemblies can be introduced into the heart either surgically or percutaneously and used to deliver blood from one location in the heart or circulatory system to another location in the heart or circulatory system. For example, when deployed in the heart, an intracardiac pump can pump blood from the left ventricle of the heart into the aorta, or pump blood from the right ventricle to the pulmonary artery. Intracardiac pumps can be powered by a motor located outside of the patient's body or a motor located inside the patient's body. Some intracardiac blood pump systems can operate in parallel with the native heart to supplement cardiac output and partially or fully unload components of the heart. Examples of such systems include the IMPELLA® family of devices (Abiomed, Inc., Danvers Mass.).

A blood pump system includes a pump and a compartment. A catheter is attached at one end to the pump and at the other end to the compartment. The catheter typically includes multiple fluid lumens which carry liquid to the pump in a distal direction. The compartment may be multifunctional. In some adaptations, it includes mechanical components and electronics that enable the pump to operate and be maintained. Leaks from lumens within the catheter may reach the compartment and compromise electronic elements within the compartment. Leaks may lead to, for example, pump stoppage or a decrease in overall system pressure.

SUMMARY

Systems, methods and devices are described herein for preventing leaks in an intracardiac blood pump system. Such a system can prevent egress of fluid from a catheter into a compartment of the blood pump system that contains electronic elements, while maintaining functionality of the pump. A filter, as described herein, is placed advantageously between the catheter of the blood pump system and the compartment to differentially seal the compartment. For example, the filter permits sterilization gas to pass through the filter to the catheter, but prevents liquid from the catheter (e.g., as the result of a leak) from passing through the filter and into the compartment.

In some implementations, the intracardiac blood pump system comprises a pump, a catheter proximal of the pump, a compartment proximal of the catheter, a conduit extending through an interface between the compartment and the catheter, and a filter within the conduit. For example, the blood pump system may be an Impella® device of Abiomed, Inc. or any other suitable system. In some implementations, a controller is configured to facilitate operation of the blood pump systems described herein. For example, the controller may be the Automated Impella Controller (AIC)® of Abiomed, Inc. or any other suitable controller that receives input signals and translates them into operational signals to operate the pump. At least one advantage of a separate controller configured to facilitate operation of the intracardiac blood pump systems is precise control of the system and to acquire data related to the system.

In some implementations, the pump comprises a housing and a rotor disposed within the housing. The rotor may have at least one blade. Specifically, the rotor may include an impeller blade shaped to induce fluid flow when under rotational force. In some implementations, the rotor is driven by an implantable motor having a rotor and stator. A proximal end of the rotor may be coupled to a drive shaft. In some implementations, the motor is external to the patient and drives the rotor by an elongate mechanical transmission element, such as a flexible drive shaft, drive cable, or a fluidic coupling.

In some implementations, the catheter is an elongate multi-lumen catheter having a proximal end, a distal end and a central lumen. The distal end of the elongate multi-lumen catheter may be adjacent the pump housing. For example, when the blood pump system is in use, the pump housing is placed inside a patient's heart and the elongate multi-lumen catheter may extend from the patient's heart and through the patient's vasculature such that a first portion of the catheter is within the patient and a second portion of the catheter is outside of the patient. The catheter may comprise two, three, four, five or any suitable number of lumens. For example, two separate tubes may pass through the central lumen of the catheter, thus defining three lumens total—the first central lumen, a lumen through the first tube and a lumen through the second tube. Some lumens may extend an entire length of the catheter, while other lumens may extend only partially through the catheter.

In some implementations, the compartment is proximal of the proximal end of the catheter. For example, a distal end of the compartment may be located adjacent the proximal end of the catheter. At least one advantage of positioning the compartment adjacent the proximal end of the catheter is that tubing may extend through the compartment and enter a lumen of the catheter. In some examples, the catheter can partially extend within the compartment (e.g., to provide structural support at the connection point between the catheter and the compartment). In some examples, the proximal end of the catheter abuts the distal end of the compartment.

In some implementations, the blood pump system further comprises a connector at the interface between the compartment and the catheter. The first lumen and the conduit may pass through the connector. In some implementations, the connector has an inner volume and the filter fills at least 50 percent of the inner volume of the connector. In some examples, the connector extends partially into the compartment. In some examples, the catheter extends partially into the connector. At least one advantage of providing a connector between the compartment and the catheter is to provide additional structural stability at the connection point between the two elements. For example, the connector may prevent the catheter from bending sharply or kinking where it connects to the compartment.

In some implementations, the compartment comprises a first opening and one or more side ports. The first opening of the compartment may be located at a distal end of the compartment and connect to the proximal end of the catheter. The one or more side ports of the compartment may be located proximal of the first opening of the compartment. For example, there may be one or two side ports located between distal and proximal ends of the compartment. At least one advantage of providing side ports is to allow fluid-carrying lumens to enter into the compartment and then extend into the proximal end of the catheter. In particular, the side ports provide connections to external fluid sources that may provide fluid through the catheter to a pump or patient.

In some implementations, there is at least one electronic element within the compartment. The at least one electronic element may comprise a memory, a pressure transducer and/or a pressure sensor. For example, a printed circuit board comprising transistors, inductors, resistors, capacitors, sensors or any other suitable element may be disposed within the compartment. The electronics within the compartment may also allow for the pump to be connected to a pump controller. At least one advantage of including a memory element within the compartment is that the blood pump system may store operating parameters for use if the pump is connected to multiple controllers at different points in time. At least one advantage of including a pressure transducer and/or pressure sensor within the compartment is that the pump system may "translate" pressure readings (e.g., from a pressure transducer) such that a pressure signal or related parameter can be sent to a controller and displayed for a user.

In some implementations, a first lumen of the elongate multi-lumen catheter is configured to carry fluid from an external source. The fluid may be carried through the one or more side ports of the compartment and through the first opening of the compartment to the distal end of the elongate multi-lumen catheter. In some implementations, the first lumen passes through the compartment. For example, the first lumen may be defined by a first end point external to the compartment, extend through a portion of the compartment, into the catheter and terminate at a second end point within the catheter or at the distal end of the catheter. In some implementations, the first lumen is within the central lumen. At least one advantage of placing the first lumen within the central lumen is to provide a single tube comprising all other tubes extending from the compartment to prevent tangling and/or kinking of tubing. Additionally, by placing the first lumen within the central lumen, the first lumen is protected from external forces (e.g., nicks, etc.) by an extra layer of tubing.

In some implementations, the fluid is blood, saline, purge fluid, glucose, heparin or any other suitable material or combination thereof. For example, the fluid may comprise dextrose and heparin. In some implementations, the fluid comprises purge fluid, which flows through the first lumen to the rotor to maintain the pump substantially free of blood. At least one advantage of using a purge fluid is that the flow of the purge fluid can provide a barrier against blood ingress into the gap between the rotor and motor stator or pump housing which could otherwise cause damage to the blood (e.g., hemolysis) or damage to the motor (e.g., increased friction, overheating, and/or seizing). For example, the purge fluid may comprise dextrose and heparin. At least one advantage of using a combination of dextrose and heparin is preventing the formation of blood clots (e.g., via anticoagulant heparin) with an appropriate amount of active agent while maintaining biocompatibility and flow.

In some implementations, the blood pump system further comprises a second lumen of the elongate multi-lumen catheter. The second lumen may be configured to carry a second liquid. In some examples, the second lumen extends through the compartment. The second fluid may be also carried from an external source through the one or more side ports of the compartment and through the first opening of the compartment to the distal end of the elongate multi-lumen catheter. In some examples, the second lumen is a pressure lumen and the second fluid is saline. The second lumen may have an opening located distal the compartment. At least one advantage of a second lumen is that the second lumen may carry a fluid different from the first lumen and that may be provided via a different external source. For example, the first lumen may carry purge fluid while the second lumen carries saline, and the purge fluid and the saline may be maintained separate from one another.

In some implementations, the conduit extends through the interface between the compartment and the multi-lumen catheter. The conduit may comprise a first end located proximal of the first opening of the compartment and a second end located distal of the first opening of the compartment, such that the conduit spans the first opening of the compartment. Positioning the conduit within both the compartment and the catheter allows a liquid or gas to be inserted into the catheter from the compartment and therefore provides access to the central lumen of the catheter. The conduit is configured to carry gas from the first end of the conduit through the first opening of the compartment to the second end of the conduit. The second end of the conduit may be in fluid communication with the central lumen of the elongate multi-lumen catheter. For example, a proximal end of the conduit may extend a short ways into the compartment and a distal end of the conduit may extend a short ways into the catheter. The system may be immersed in an environment filled with gas, introduced via an external gas source, and the conduit may allow for penetration of the gas to the interior of the catheter. At least one advantage of carrying gas to the interior of the catheter is to sterilize the central lumen of the catheter such that any fluid (e.g., that may come into contact with a patient) within the catheter is maintained sterile.

In some implementations, the filter is disposed within the conduit. The filter may be configured to prevent egress of the fluid from the multi-lumen catheter into the compartment, while allowing flow of gas from the first end of the conduit through the second end of the conduit and into the multi-lumen catheter. At least one advantage of placing the filter within the conduit is that any fluid leak from within the central lumen of the catheter will reach the filter (via the conduit) before reaching any electronic elements within the compartment.

In some implementations, the gas carried by the conduit is sterilization gas. The sterilization gas may be used to sterilize the central lumen. For example, the gas may be ethylene oxide, nitrogen dioxide, ozone, vaporized hydrogen peroxide or any other suitable gas. At least one advantage of using sterilization gas is to sterilize the central lumen of the catheter such that any fluid (e.g., that may come into contact with a patient) within the catheter is maintained sterile.

In some implementations, the filter is configured to prevent a leak of liquid from the central lumen passing through the conduit and reaching the compartment in some situations. During operation of the blood pump system, the first lumen may be damaged such that liquid leaks from the first lumen into the central lumen of the catheter. For example, purge fluid may leak from a lumen into the central lumen of the catheter. Without the filter, the leaked liquid would flow from the catheter into the compartment which would be problematic. But the filter located in the conduit prevents the leaked liquid from reaching the interior of the compartment, and thus prevents the fluid from reaching the at least one electronic element. To achieve a proper seal but still facilitate sterilization, the filter is configured to provide liquid filtering, so it allows a flow of gas to be carried across the filter prior to any liquid contact. At least one advantage of preventing leaks from passing through the filter is to prevent liquid from reaching electronic elements within the compartment. For example, if liquid were to contact any exposed electronic elements within the compartment, the liquid could cause a short or otherwise damage the electronics, causing pump operation to stop or change. At least one advantage of allowing gas to pass through the filter is to allow the central lumen of the catheter to be sterilized.

Positioning the filter can help achieve the liquid seal. In some implementations, the filter is located proximal of the first opening of the compartment. For example, the filter may be placed wholly within the compartment. In some implementations, the filter is located distal of the first opening of the compartment. For example, the filter may be placed wholly outside of the compartment. In some implementations, the filter extends across the first opening of the compartment. In some implementations, a portion of the filter extends within the compartment. For example, the filter may span the first opening of the compartment such that a first portion of the filter is within the compartment and a second portion of the filter is outside of the compartment. At least one advantage of placing the filter such that it extends across or near an opening of the compartment is that the filter may prevent liquid from contacting the interior of the compartment (and electronic elements located therein).

In some implementations, the filter comprises a hydrogel adhered to pore walls of a porous substrate. The filter may be, for example, a filter such as that described in US Patent Publication 2004/0052689, which is hereby incorporated by reference in its entirety. The hydrogel may be hydrophilic polyurethane, hydrophilic polyuria, hydrophilic polyureaurethane or any suitable material. At least one advantage of using a hydrogel (e.g., a hydrophilic polymer) is that a hydrogel swells in aqueous solutions and retains a significant fraction of aqueous solution it is exposed to without dissolving. The porous substrate may be metal, ceramic, glass, organic, non-organic, organic polymers, acrylic polymers, polyolefins or any suitable material or combination thereof. At least one advantage of a porous substrate is that it has channels through which gas can flow, which facilitates sterilization. At least one advantage of using a filter comprising a hydrogel and a porous substrate is that the filter may prevent contamination between two portions of tubing when the filter is placed between the portions and by blocking the flow from aqueous solution between the two portions.

In some implementations, the filter self-seals when exposed to liquid. For example, the filter may self-seal when exposed to aqueous medium. In some implementations, the filter is gas-permeable. In some implementations, the self-sealing filter responds (i.e., seals) quickly when exposed to liquid, causes little or no contamination of liquid solutions with which it comes in contact, and is capable of withstanding high back-pressures (e.g., greater than about 7 psi) before again allowing the passage of gas or liquid. In some implementations, the filter is biocompatible. At least one advantage of a self-sealing filter is short response time, little or no contamination of aqueous solutions with which they come in contact, and the ability to withstand high back-pressures.

In some implementations, the filter is in the shape of a narrow cylinder, the filter being sized and shaped to fit within the conduit. In some implementations, the conduit may be a narrow tube. The filter may have an outer diameter equal to an inner diameter of the conduit, such that the filter fits snuggly within the conduit. In some implementations, the filter is in the shape of a frustum, the filter being sized and shaped to fit within the conduit. The filter may have a first outer diameter equal to an inner diameter of the conduit, such that the filter fits snuggly within the conduit at a first end, and then tapers to follow the shape of the conduit. At least one advantage of shaping and sizing the filter to fit snuggly within the conduit is that any gas or liquid passing through the conduit will come into contact with the filter, and the filter may thus prevent liquid from flowing from one end of the conduit to the other (e.g., from the central lumen of the catheter to the interior of the compartment). The filter may have any other shape (e.g. disc, prism, etc.) that accommodates a shape of the conduit.

In some implementations, manufacturing a filter for a blood pump system (such as the systems described herein) comprises coating filter media of a support material with a hydrogel. For example, the filter media may be fibers, granules, powder, or any other suitable substance. At least one advantage of using a filter comprising a hydrogel and filter media is that when placed between two portions of a conduit, the filter permits gas flow between the two portions to allow sterilization inside one of the portions, and may prevent liquid contamination if an aqueous solution attempts to flow between the two portions. The blood pump system comprises a catheter defining at least one lumen having a lumen cross section. The coated filter media can be assembled to form a self-sealing filter, sized and shaped to have a cross section equal to that of the lumen cross section. At least one advantage of thus assembling the filter is to ensure the filter fits snuggly within the lumen such that it can block or impede any gas or liquid passing through the conduit. The self-sealing filter may be positioned at a distal end of a sealed compartment. An elongate catheter (defining a lumen) is positioned such that the self-sealing filter extends between the sealed compartment and a portion of the elongate catheter. The filter may thus prevent liquid from flowing from one end of the conduit to the other (e.g., from the central lumen of the catheter to the interior of the compartment). A sterilization gas is delivered to the elongate catheter via a hollow tube extending through at least a portion of the sealed compartment. At least one advantage of using sterilization gas is to sterilize the central lumen of the catheter such that any fluid (e.g., that may come into contact with a patient) within the catheter is maintained sterile.

In some implementations gas is allowed to penetrate through a conduit to sterilize a central lumen of a multi-lumen catheter. The conduit is positioned across the first opening of the compartment. The compartment is positioned adjacent a proximal end of the catheter. Fluid is passed through the first lumen from an external source to the distal end of the multi-lumen catheter. A self-sealing filter prevents egress of the fluid from the multi-lumen catheter into the compartment while allowing the flow of gas from the first end of the conduit to the second end of the conduit. At least one advantage of preventing leaks from passing through the filter is to prevent liquid from reaching electronic elements within the compartment. If liquid were to contact any exposed electronic elements within the compartment, the liquid could cause a short or otherwise damage the electronics, causing pump operation to stop or change. At least one advantage of allowing gas to pass through the filter is to allow the central lumen of the catheter to be sterilized.

DETAILED DESCRIPTION

To provide an overall understanding of the systems, method and devices described herein, certain illustrative embodiments will be described. Although the embodiments and features described herein are specifically described for use in connection with a percutaneous blood pump system, it will be understood that all the components and other features outlined below may be combined with one another in any suitable manner and may be adapted and applied to other types of cardiac therapy and cardiac assist devices, including cardiac assist devices implanted using a surgical incision and the like. Additionally, though the application of pump elements has been described here with regard to blood pumps, it is to be understood that the pump elements may be applied to other pumps for which any type of fluid flow being sent distally can flow proximally and damage electronic components. For example, pumps which are used in acidic or otherwise corrosive environments may require a purge flow to prevent the ingress of acid which would be damaging to pump components. Although the embodiments and features described herein are specifically described for use in connection with an intracardiac blood pump system, it will be understood that a blood pump system according to the embodiments and features described herein may be used within any vasculature and/or in combination with other systems. For example, the filter systems and placement described below may be used in urethra or bladder catheterization systems; right heart cardiac support systems; intra-aortic balloon pumps; extracorporeal membrane oxygenation devices; left ventricular assist devices; renal support systems, such as cardiac assist devices to adjust kidney autoregulation; infusion systems; central venous catheters; or any other suitable system.

Figure 1:
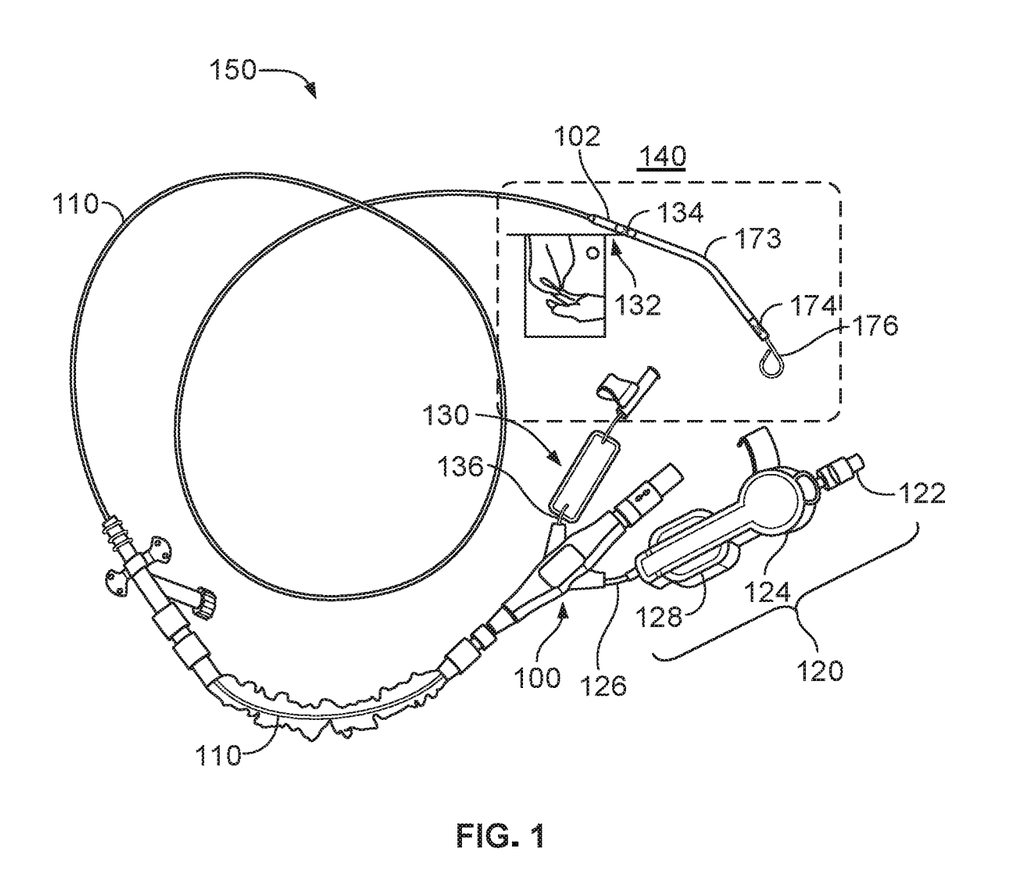
FIG. 1 shows an illustrative blood pump system, according to certain implementations.

FIG. 1 shows an intracardiac blood pump system 150 for use with filters such as filters 216 and 316, described further below in relation to FIGS. 2 and 3. The system 150 includes an elongate catheter body (also referred to as an elongate multi-lumen catheter) 110, a pump 140, a compartment 100, a purge side arm 120 and a pressure side arm 130. Purge side arm 120 includes fitting 122, pressure reservoir 124, infusion filter 128, and tube 126. Pressure side arm 130 includes tube 136. Pump 140 includes a pump housing 134, a motor housing 102, a cannula 173, a suction head 174 and a flexible projection 176. Pump 140 can be inserted into a patient's body through a variety of methods.

The methods through which pump 140 can be inserted into a patient include, but are not limited to, using an over-wire technique and a side-rigger technique. For example, a first guidewire is inserted into the vasculature of the patient and a guide catheter is then threaded over the first guidewire. The first guidewire is in turn removed, allowing for the introduction of a second guidewire within the guide catheter. For example, the second guidewire is stiffer than the first guidewire, to facilitate the backloading of the pump onto the guidewire. Once the stiffer guidewire is in place, the pump is threaded over the wire, using either the standard over-wire technique or the side-rigger technique. The guide wire is removed prior to pump operation. Alternatively, the guide wire is not removed prior to operation. Alternatively, the pump can be backloaded over a guidewire inserted through the free space of the pump impeller. In one implementation, an easy-guide lumen 132, as described for example in U.S. Pat. Nos. 8,814,776; 9,402,942; and 9,750,861, incorporated by reference herein in their entirety, can be used in combination with the guide wire to more easily backload the pump with the guide wire passing through the free space of the impeller, and without damaging the impeller. Easy guide-lumen 132 is removed prior to operating the pump, as is the guide wire. In another implementation, the pump is backloaded over the guidewire without the use of an easy guide lumen.

In some implementations, purge fluid is delivered to a rotor in pump 140 to maintain the pump substantially free of blood. As detailed below, at least one advantage of using a purge fluid is that the flow of the purge fluid can provide a barrier against blood ingress into the gap between the rotor and motor stator or pump housing which could otherwise cause damage to the blood (e.g., hemolysis) or damage to the motor (e.g., increased friction, overheating, and/or seizing). Purge fluid may be delivered through a first lumen (e.g., as defined by tube 512 of FIG. 5) of the elongate catheter body 110 through the motor housing 102 to a proximal end of the cannula 173. The first lumen of the elongate catheter body 110 supplies the purge fluid to the pump 140 from a fluid reservoir (not shown) via purge side arm 120. Tube 126 partially defines the first lumen of the elongate catheter body 110. The first lumen passes through compartment 100 (e.g., compartments 200, 300, and 500 FIGS. 2, 3 and 5, respectively) and into the elongate catheter body 110 and may include connectors or fittings.

In some implementations, the motor is "onboard," as shown in FIG. 1, and may be located within the patient's body during operation of the pump and be configured with electrical leads that transmit power to the motor for driving the pump. As mentioned previously, the motor can alternatively be located outside of the patient's body and can actuate the rotor via a drive shaft, drive cable, or drive line. For example, the motor may be located within a handle (e.g., connected to compartment 100) of the pump system. In some examples, a drive cable may extend through elongate catheter body 110 to a rotor located near a proximal end of cannula 173. In some implementations, the drive shaft, drive cable, or drive line operate in combination with the purge fluid delivery (e.g., through tube 512 of FIG. 5) described herein.

The purge fluid flows through the pump to prevent ingress of blood cells into the pump. Alternatively or additionally, the purge fluid may function as a lubricant for bearings of the pump (not shown) or as a coolant to dissipate heat produced by electromagnetic motor coils of the motor stator. The purge fluid may be lubricant, coolant, medicine or any suitable hemocompatible fluid. For example, the purge fluid may be saline, Ringer's solution, glucose solution, heparin or any other suitable fluid. The purge fluid prevents blood from entering the motor housing 102 during operation of the pump 140. The purge fluid may also prevent ingress of blood into the elongate catheter body 110. In some implementations, a highly viscous purge fluid, such as a glucose solution, is used to lubricate bearings internal to the pump 140. In other implementations, pharmacological agents are used as a purge fluid to purge the pump of blood, as well as perform a medical purpose. For example, the purge fluid may include heparin to prevent blood clotting. The purge fluid flows through a first lumen of the elongate catheter body 110 and flows out of the pump 140 at the outlet openings near the proximal end portion of pump 140. The purge fluid is safely dispersed into the blood stream of the patient.

Another lumen (e.g., as defined by tube 516 of FIG. 5) of the elongate catheter body 110 could supply a pressure fluid to the pump via pressure side arm 130. Pressure side arm 130 provides fluid to a fluid-filled pressure lumen with an inlet at the proximal end of the motor housing 102. The fluid-filled pressure lumen, in combination with an electronic element located in compartment 100, may be used to determine the placement of the pump relative to the aortic valve of a patient. For example, the electronic element may be a pressure transducer that "translates" pressure from the pressure lumen into a value that can be output to an external system or display. In some implementations, a second fluid reservoir or pressure bag (not shown) is connected to the proximal end of pressure side arm 130 to provide the pressure fluid. The pressure fluid may be the same as or different than the purge fluid. For example, the pressure fluid may be saline, Ringer's solution, glucose, heparin, or any hemocompatible fluid.

In some implementations, the blood pump system 150 includes an optical pressure sensor (e.g., a Fabry-Perot optical pressure sensor) located distal of the motor. An optical fiber extends proximally from the optical pressure sensor along the catheter. The optical pressure sensor includes a cavity that is terminated by a thin, pressure sensitive glass membrane. The light exiting from the optical fiber is reflected by the glass membrane and into the optical fiber. The reflected light is transmitted along the length of the optical fiber to electronic control elements (e.g., within compartment 100 or within a connecting console), which determines a pressure signal based on an interference pattern in the reflected light.

Side ports of compartment 100 allow fluidic connections to compartment 100, as described in greater detail below in relation to FIG. 5. Purge side arm 120 and pressure side arm 130 connect to compartment 100 at a first side port (e.g., tube 526 of FIG. 5) and a second side port (e.g., tube 524 of FIG. 5), respectively. The first lumen (partially defined by tube 126) and the second lumen (partially defined by tube 136) extend through compartment 100 to enter the elongate catheter body 110. In some implementations, tube 126 joins a tube (e.g., tube 512 of FIG. 5) within compartment 100 at a glue connection at or near the first side port, such that the first lumen extends through tube 126, through compartment 100 and through the elongate catheter body 110 to deliver purge fluid to pump 140. In some implementations, tube 136 similarly joins a different tube (e.g., tube 516 of FIG. 5) within compartment 100 at a glue connection at or near the second side port, such that the second lumen extends through tube 136, through compartment 100 and through the elongate catheter body 110 to deliver pressure fluid to pump 140.

In some implementations, the first lumen and the second lumen of the elongate catheter body 110 are maintained separate from one another. The first and second lumens may extend through a central lumen of the elongate catheter body 110, and be configured to carry fluid while the central lumen of the elongate catheter body 110 remains free of purge and pressure fluid. The central lumen of the elongate catheter body 110 may, however, carry fluid in the case of a leak from either the first or second lumens. For example, during operation of the pump, the first lumen may be kinked or accidentally damaged such that purge fluid leaks out of the first lumen into the central lumen of the elongate catheter body 110. In the case of a leak reaching the central lumen of the elongate catheter body 110, two potentially problematic situations can arise: (1) the leaking fluid may reach the patient (e.g., through inlets and outlets provided in pump 140) and (2) the leaking fluid may reach the interior of compartment 100.

To reduce or eliminate the chance of danger to a patient in the case of leaking fluid in the central lumen of the elongate catheter body 110, the central lumen is sterilized using a sterilization gas. The fluids in the first lumen (purge fluid) and the second lumen (pressure fluid) are hemocompatible and thus a leak from the first lumen or second lumen does not pose a patient risk on its own, unless the fluid is contaminated (e.g., via germs in the central lumen). Because of this potential risk, the central lumen is sterilized even though fluid does not ordinarily flow through the central lumen to reach the pump 140.

To sterilize the central lumen, sterilization gas enters the central lumen of the elongate catheter body 110 via a conduit (e.g., conduit 214 of FIG. 2, conduit 314 of FIG. 3) that the extends through an opening of compartment 100 and into the elongate catheter body 110. The conduit comprises a proximal end located proximal of the first opening of the compartment 100 and a distal end located distal of the first opening. The proximal end of the conduit 214 may be accessed, for example, through the interior of compartment 100 prior to final assembly of the blood-pump system. By inserting sterilization gas through the proximal end of the conduit, the sterilization gas reaches the central lumen of the elongate catheter body 110. In the event that purge fluid or pressure fluid leaks into the central lumen, the leaked liquid will remain sterile because of the sterilization gas. At least one advantage of sterilizing the central lumen is that if any leaked liquid reaches the patient (e.g., through the distal end of intracardiac blood pump system 150), the fluid is still sterile and will not introduce bacteria into the patient.

Because the proximal end of the conduit is located within the interior of compartment 100 while the distal end of the conduit is located within the central lumen of the elongate catheter body 110, in the event that liquid leaks into the central lumen of the elongate catheter body 110, the leaked liquid could potentially reach the conduit. To prevent the leaked liquid from reaching the interior of compartment 100 (and the electronic elements disposed therein) through the conduit, a self-sealing filter (e.g., filter 216 of FIG. 2, filter 316 of FIG. 3) is placed within the conduit (e.g., conduit 214 of FIG. 2, conduit 314 of FIG. 3). The self-sealing filter prevents liquid from flowing in at least one direction through the conduit, while allowing gas to flow through the conduit The self-sealing filter allows gas to flow through the conduit but prevents liquid from flowing in at least one direction through the conduit, by sealing when in contact with liquid. Thus, sterilization gas to which the device is exposed to prior to any liquid exposure is allowed to reach the central lumen of the elongate catheter body 110 through the conduit, but any leaked liquid within the central lumen of the elongate catheter body 110 cannot reach the interior of compartment 100. Various implementations of filters and blood pumps assemblies are further described below in relation to FIGS. 2-5.

Figure 2:
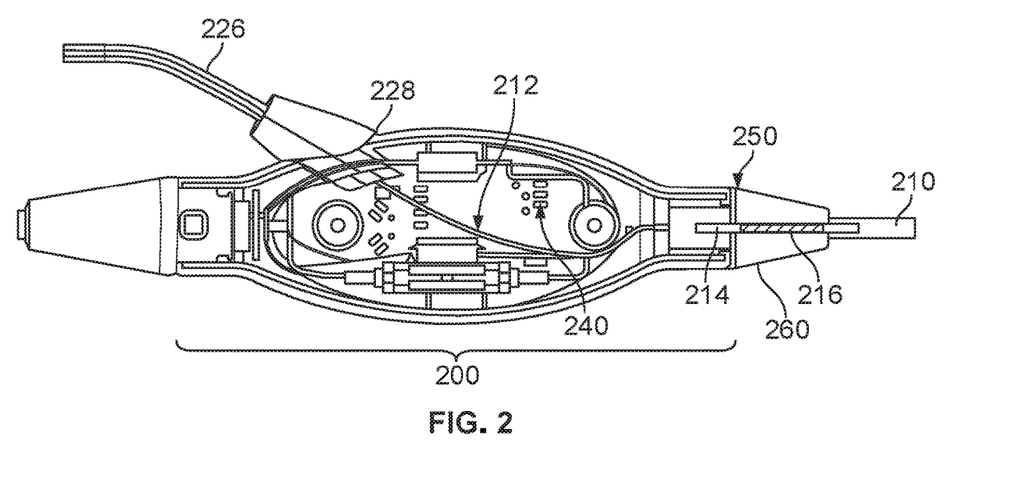
FIG. 2 shows a compartment with one side port, according to certain implementations.

FIG. 2 shows a compartment 200 with one side port 228, according to certain implementations. Compartment 200 is similar to compartment 100 of FIG. 1 but comprises a single side port for a purge arm, rather than the two side arms described above. The compartment 200 is connected to a catheter 210 with a self-sealing filter 216 to prevent fluid leaks from the catheter 210 reaching the interior of the compartment 200. For example, the compartment may be the Impella® plug of Abiomed, Inc. A first lumen defined by tubes 226 and 212 extends from outside of compartment 200 and through side port 228. Tube 226 may be, for example, similar to tube 126 described above in relation to FIG. 1 and may be part of a purge side arm similar to purge side arm 120. The first lumen passes through a portion of the interior of compartment 200, extends through the first opening 250 of the compartment and extends through connector 260 to enter catheter 210. In some embodiments, tube 212 extends through first opening 250 and through the length of catheter 210. In some embodiments, connector 260 is a plastic component configured to provide support to the proximal end of the catheter 210.

Conduit 214 extends through opening 250, through connector 260 and into catheter 210. As described above, conduit 214 may allow gas to penetrate the central lumen of catheter 210. For example, the gas may be a sterilization gas configured to sterilize the central lumen of catheter 210. Conduit 214 is in the shape of a narrow cylinder and a length relatively short compared to a length of catheter 210. The proximal end of conduit 214 is located within compartment 200 and proximal of opening 250. The distal end of conduit 214 is located within catheter 210 and distal of opening 250. In some embodiments, conduit 214 is in fluid communication with the central lumen of catheter 210. Conduit 214 is shown as a cylindrical tube. However, conduit 214 may be a frustum, a narrow cylinder, a curve cylinder, a rectangular prism or any suitable shape.

Filter 216 is located within conduit 214. In some implementations, filter 216 is in the shape of a narrow cylinder. In some implementations, filter 216 is sized and shaped to entirely fill an internal diameter of conduit 214, such that gas or liquid flowing through conduit 214 will encounter filter 216, as described in further detail below in relation to FIG. 5. Filter 216 allows gas to flow from the proximal end of conduit 214 to the distal end of conduit 214, but prevents liquid from the distal end of conduit 214 from reaching the proximal end of conduit 214. This configuration allows gas (e.g., sterilization gas) to reach the central lumen of catheter 210 prior to any exposure to liquid but prevents a liquid (e.g., leaked purge fluid, as described above) from reaching within compartment 200. Conduit 214 and filter 216 are placed such that purge fluid flowing through the first lumen defined by tubes 226 and 212 does not pass through conduit 214 and, as such, does not encounter filter 216. Thus, purge fluid may still reach a pump (e.g., pump 140) through catheter 210, without being blocked by filter 216.

At least one electronic element 240 is disposed within compartment 200. Electronic element 240 may include pressure transducers, pump-control circuitry, resistors, capacitors, inductors, transistors, wiring or any other suitable element. Other electronic elements, for example, elements of printed circuit boards (PCBs), may also be disposed within compartment 200. The proximal end of compartment 200 (located opposite of opening 250) may, for example, be connected to a power supply configured to power electronic elements 240. If liquid (e.g., leaked purge fluid from the first lumen that has reached the central lumen of catheter 210) enters the interior of compartment 200, it can short or otherwise damage electronic elements 240. For example, if the electronic elements corrode due to fluid damage, pump operation and functionality may be damaged or may stop completely, which can be dangerous for a patient. Filter 216 prevents fluid from reaching the electronic elements. In some implementations, filter 216 is impermeable to liquid but permeable to gas. Because filter 216 is sized and shaped to fill the internal diameter of conduit 214, liquid that may otherwise flow through conduit 214 (e.g., purge fluid that has leaked into the central lumen of catheter 210) will instead be "blocked" by filter 216. Because filter 216 is within conduit 214 (which extends between catheter 210 and compartment 200), liquid is effectively blocked from reaching the interior of compartment 200 (which holds electronic elements 240) via the conduit 214.

Figure 3:
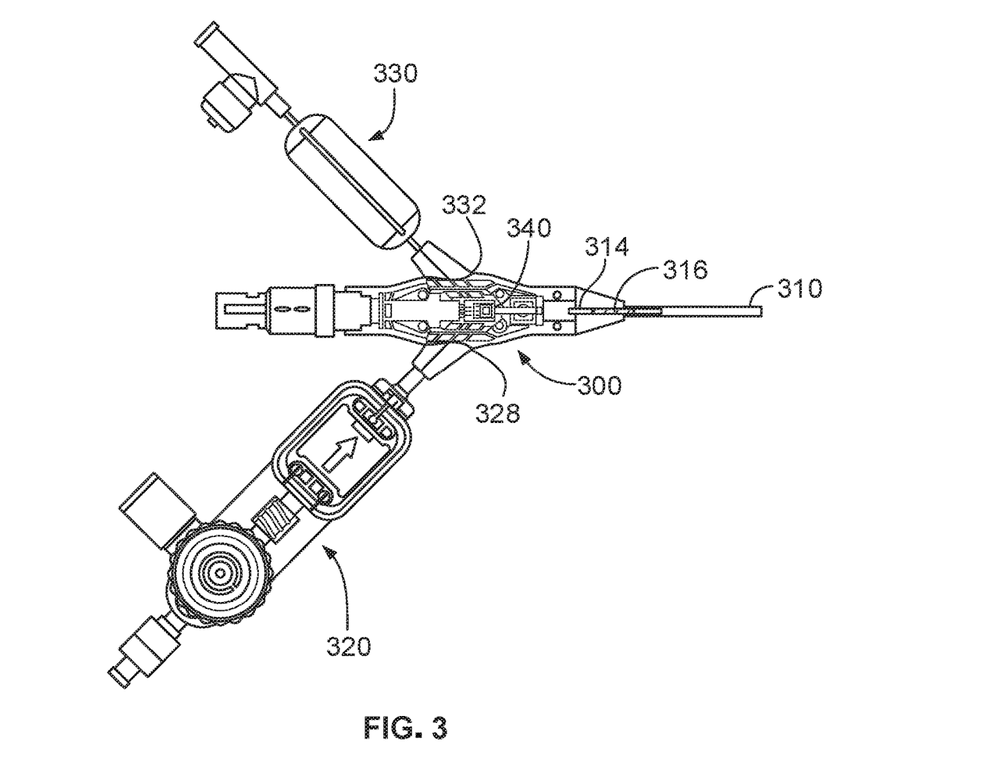
FIG. 3 shows a compartment with two side ports, according to certain implementations.

FIG. 3 shows a compartment 300 with two side ports, according to certain implementations. FIG. 3 is similar to FIGS. 1 and 2 described above. In relation to FIG. 1, pressure side arm 330 corresponds to pressure side arm 130, purge side arm 320 to purge side arm 120, catheter 310 to the elongate catheter body 110. In relation to FIG. 2, electronic elements 340 correspond to 240, side port 328 to side port 228, conduit 314 to conduit 214, and filter 316 to filter 216. FIG. 3 differs from FIG. 2 in that FIG. 3 has an additional side port 332. Side port 332 allows for the connection of pressure side arm 330, such as pressure side arm 130 described above in relation to FIG. 1.

Figure 4A:
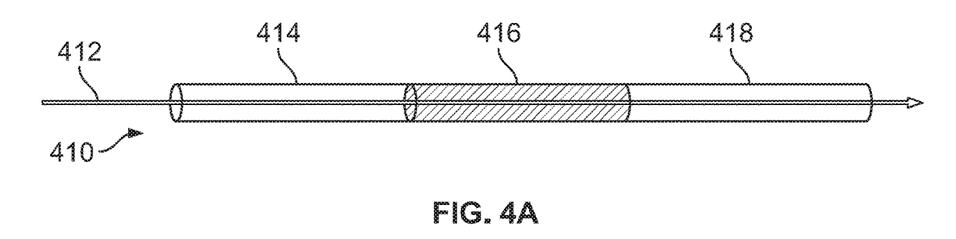
FIG. 4A-C show a self-sealing filter allowing sterilization gas to pass through and a self-sealing filter preventing the flow of liquid, according to certain implementations.
Figure 4B:
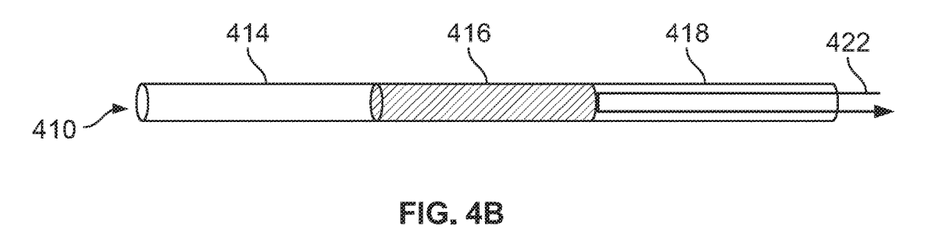
Figure 4C:
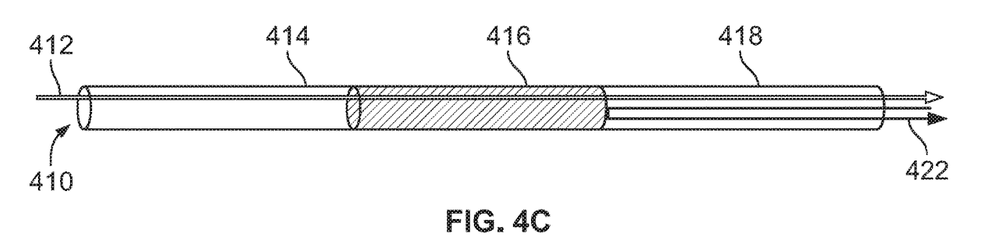

FIGS. 4A-C show a semi-permeable filter, according to certain implementations. FIG. 4A show a semi-permeable filter 416, allowing a flow of gas indicated by arrow 412 to pass through a conduit 410, prior to any contact with liquid. Gas flow indicated by arrow 412 enters and passes through a proximal portion 414 of conduit 410, then passes through filter 416, then passes through a distal portion 418 of conduit 410. FIG. 4B shows filter 416 preventing a flow of liquid indicated by arrow 422 from passing through conduit 410. The flow of liquid indicated by arrow 422 enters a distal portion 418 of conduit 410, encounters resistance at filter 416 such that the flow of liquid cannot permeate filter 416 and reach proximal portion 414. Instead, the flow of liquid exits conduit 410 through distal portion 418. The flow of liquid indicated by arrow 422 does not reach a proximal portion 414 of conduit 410 because the material properties of filter 416 cause the elements of filter 416 to swell such that liquid cannot pass through the entire length of the filter. FIG. 4C shows filter 416 allowing the flow of gas indicated by arrow 412 to pass through conduit 410 while preventing the flow of liquid indicated by arrow 422 from passing through conduit 410. As shown in FIG. 4C, in some implementations, filter 416 may simultaneously allow the flow of gas while preventing the flow of liquid across conduit 410. In some implementations, filters 416 self-seals when exposed to liquid. In some implementations, when filter 416 has sealed in response to encountering liquid, filter 416 is also fully or partially sealed against the flow of gas. For example, if the filter media of filter 416 swells to prevent the flow of liquid through conduit 410, the swollen filter media may also prevent the flow of gas through conduit 410. In some implementations, filter 416 is permeable to gas but impermeable to liquid.

In some implementations, filter 416 may include a hydrogel that can adhere to pore walls of a porous substrate. The hydrogel may be hydrophilic polyurethane, hydrophilic polyuria, hydrophilic polyureaurethane or any suitable material. A hydrogel is a material that swells in water and retains a significant fraction of water without dissolving in water.

The porous substrate may be metal, ceramic, glass, organic, non-organic, organic polymers, acrylic polymers, polyolefins or any suitable material or combination thereof. Porous substrates from which filter 416 can be made are insoluble in water and contain one or more channels or pores through which gas or liquid molecules can pass. This allows the passage of gas through the channels. The hydrogel adheres to the porous substrate. The hydrogel swells when in contact with liquid such that the liquid cannot pass through the channels. Once in contact with liquid, the filter becomes impermeable.

The mechanical, physical, and chemical properties of filter 416 can be adjusted by the appropriate selection of the substrate and hydrogel materials and the process used to make the filter material. For example, small diameter pores or channels may be used when rapid self-sealing is desirable. Large diameter pores or channels may be used when smaller pressure gradients across the self-sealing filter is desired. The hydrogel may be chosen to account for the porosity and composition of the porous substrate. The porous substrate and hydrogel materials may also affect physical properties (e.g., strength, flexibility, durability, resistance to corrosion, or any other suitable property) of the filter 416, and may be chosen for the necessary physical properties in a particular application. For example, the materials of filter 416 may be chosen to match the flexibility of conduit 410. In some implementations, the material of filter 416 may be chosen for ease of implementation in small geometries (e.g., within conduit 410). In some implementations, the material of filter 416 may be chosen for its ease of forming a complete seal with conduit 410 during manufacture of the system.

In some implementations, filter 416 is selectively permeable. Filter 416 may swell, and in some cases seal to specific materials when encountering said specific materials, due to selectively attracting different kinds of molecules or bonds. For example, filter 416 may block a flow of dextrose by attracting sugar molecules, while allowing the flow of water or gas (e.g., sterilization gas). In some implementations, filter 416 may separate mixtures through chromatography (i.e., by allowing the flow of one component of the mixture through the filer, while preventing or at least greatly retarding the flow of another component of the mixture through the filter).

Figure 5:
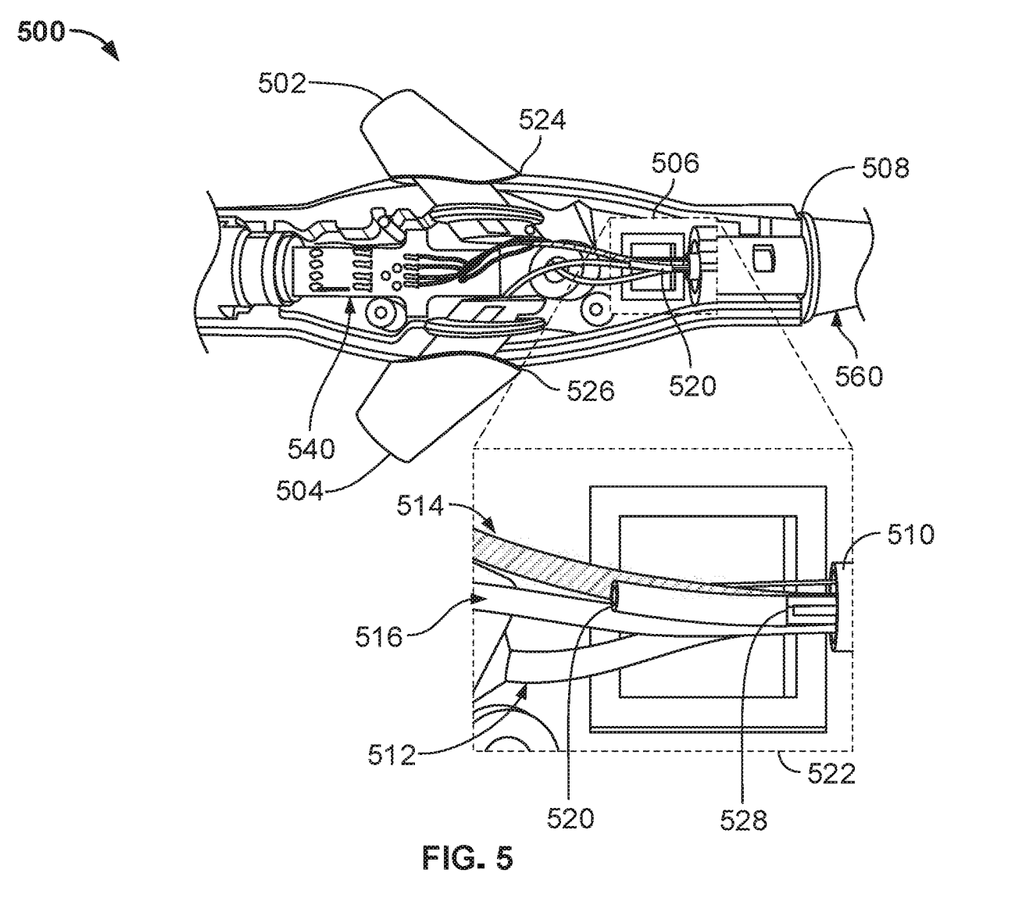
FIG. 5 shows lumens within a compartment, according to certain implementations.

FIG. 5 shows lumens within a compartment 500, according to certain implementations. FIG. 5 is similar to FIG. 3 but shows additional detail of tubing within compartment 300 as described below. Compartment 500 corresponds to compartment 300, conduit 520 corresponds to conduit 314 and catheter 510 corresponds to catheter 310. In some implementations, side joint 502 attaches a pressure side arm (e.g., pressure side arm 330) to compartment 500 through side port 524, and side joint 504 attaches a purge side arm (e.g., purge side arm 320) to compartment 500 through side port 526.

Compartment 500 may contain sensitive electronics. PCB 540 holds electronic elements (e.g., electronic elements 340) within the interior of compartment 500. Wiring extends from PCB 540 to electronics cable 514. In some implementations, electronics cable 514 is an insulated cable comprising at least one wire configured to provide power and electronic signals to a drive system of a pump (e.g., pump 140 of FIG. 1). Electronics cable 514 extends into a proximal end of a central lumen of elongate multi-lumen catheter 510. In some implementations, electronics cable 514 extends through the central lumen of catheter 510 to distal end of catheter 510.

The system of FIG. 5 includes a series of side joints and lumens that connect with compartment 500, each of which facilitates a connection, directly or indirectly, to the catheter 510. A first lumen extends through side joint 504, through side port 526, through a portion of compartment 500 and extends into a proximal end the central lumen of catheter 510. A portion of the first lumen is defined by tube 512. Tube 512 exits compartment 500 through opening 508 and extends through connector 560 (while within catheter 510). In some implementations, tube 512 extends from the proximal end of catheter 510 to a distal end of catheter 510. For example, tube 512 may terminate at a pump housing (e.g., pump housing 134 of FIG. 1) such that fluid is delivered to a rotor within the pump housing, as described below in relation to FIG. 1. In some implementations, tube 512 terminates at an opening proximal of the distal end of catheter 510. In some implementations, tube 512 extends beyond the distal end of catheter 510. In some implementations, the first lumen (partially defined by tube 512) carries purge fluid. For example, the first lumen may carry glucose, saline, heparin or any other suitable fluid.

A second lumen extends through side joint 502, through side port 524, through a portion of compartment 500 and extends into a proximal end the central lumen of catheter 510. A portion of the first lumen is defined by tube 516. Tube 516 exits compartment 500 through opening 508 and extends through connector 560 (while within catheter 510). In some implementations, tube 516 extends from the proximal end of catheter 510 to a distal end of catheter 510. For example, tube 516 may terminate at a motor housing (e.g., motor housing 102 of FIG. 1) such that fluid is delivered to a motor within the motor housing, as described below in relation to FIG. 1. In some implementations, tube 516 terminates at an opening proximal of the distal end of catheter 510. In some implementations, tube 516 extends beyond the distal end of catheter 510. In some implementations, the second lumen (partially defined by tube 516) carries pressure fluid, as described below in relation to FIG. 1. For example, the first lumen may carry glucose, saline, heparin, or any other suitable fluid.

A proximal end of conduit 520 is located within compartment 500. Conduit 520 is a hollow tube that extends within the central lumen of catheter 510, and is in fluid communication with the central lumen of catheter 510. A cross section of a proximal end of catheter 510 would show a central lumen surrounding the first lumen defined by tube 512, the second lumen defined by tube 516, electronics cable 514 and a third lumen defined by conduit 520. In some implementations, conduit 520 is significantly shorter than catheter 510. For example, conduit 520 may extend through one percent, two percent, five percent, ten percent, 20 percent, or any other suitable amount of a length of catheter 510. In some implementations, conduit 520 allows for delivery of gas to the central lumen of catheter 510 that is configured to sterilize the central lumen. For example, the proximal end of conduit 520 may be exposed to an external source of sterilization gas, such as ethylene oxide, nitrogen dioxide, ozone, vaporized hydrogen peroxide or any other suitable gas.

As shown in magnified portion 506 of the compartment 500, the third lumen defined by conduit 520 holds a filter 528 (e.g., similar to filters 416 and 426 of FIG. 4). In some implementations, filter 528 is gas permeable and/or self-seals when it comes into contact with liquid. The filter allows the sterilization gas to pass from the proximal end to the distal end of conduit 520. The filter prevents liquid from the central lumen of catheter 510 from reaching the interior of compartment 500 and the electronic components located therein. For example, if tube 512 or tube 516 is damaged and leaks purge fluid or pressure fluid into the central lumen of catheter 510, the leaked liquid will be blocked from reaching the compartment via conduit 520 by filter 528.

Figure 6:
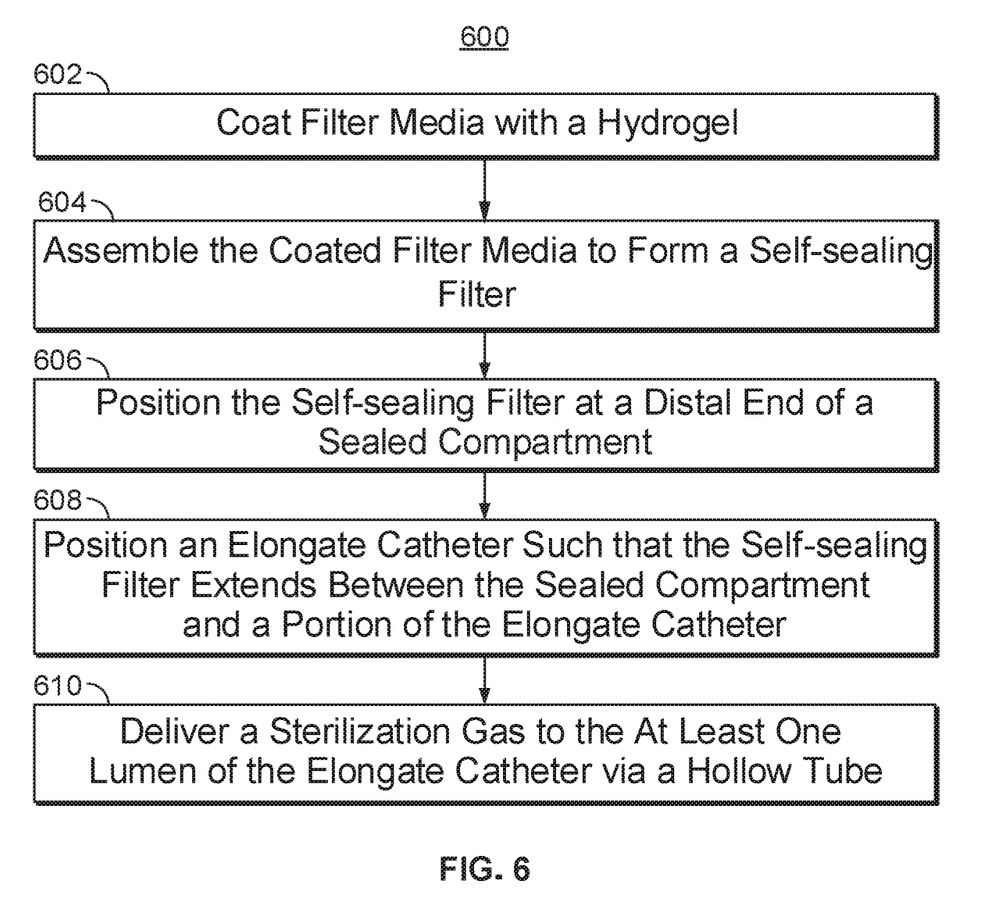
FIG. 6 shows a flowchart for manufacture of an intracardiac blood pump system with leak protection, according to certain implementations.

FIG. 6 shows a flowchart for manufacture of an intracardiac blood pump system with leak protection, according to certain implementations. Process 600 starts at step 602 where substrate of a support material are coated with a hydrogel. The hydrogel may be hydrophilic polyurethane, hydrophilic polyuria, hydrophilic polyureaurethane or any suitable material. The support material may be a porous substrate such as metal, ceramic, glass, organic, non-organic, organic polymers, acrylic polymers, polyolefins or any suitable material or combination thereof.

Process 600 continues to step 604 where the coated filter media are assembled to form a self-sealing filter. In some implementations, the coated filter media may be assembled in narrow cylindrical shape. For example, the coated filter media may be assembled to fit snuggly within a hollow tube (e.g., conduit 520 of FIG. 5). In some implementations, the coated filter media may be assembled in the shape of a frustum. For example, the filter made of the coated filter media may plug an end of a hollow tube (e.g., conduit 520 of FIG. 5). In some implementations, the size and shape of the filter are chosen to match the size and shape of the hollow tube described below. At least one advantage of fitting the filter to the size of the hollow tube is that liquid or gas flowing through the hollow tube will pass through the filter. In some implementations, the filter may fill 20 percent, 30 percent, 40 percent, 50 percent, 75 percent, 100 percent or any other suitable percentage of a length of the hollow tube. In some implementations, an outer perimeter of a cross section of the filter may be chosen to match in inner perimeter of a cross section of the hollow tube. For example, the filter may effectively plug into the hollow tube and form an aqueous liquid-seal between one end of the hollow tube from another end of the hollow tube. In some implementations, the cross section of the filter matches the cross section of the hollow tube for an entire length of the filter. In some implementations, the cross section of the filter may match the cross section of the hollow tube at a first location and differ from the cross section of the hollow tube at a second location.

Process 600 continues to step 606, where the self-sealing filter is positioned at a distal end of a sealed compartment (e.g., compartment 100 of FIG. 1). Process 600 continues to step 608, where an elongate catheter is positioned such that the self-sealing filter extends between the sealed compartment (e.g., compartment 100 of FIG. 1) and a portion of the elongate catheter (e.g., the elongate catheter body 110 of FIG. 1).

Process 600 continues to step 610, where sterilization gas is delivered to the elongate catheter via the hollow tube (e.g., conduit 520 of FIG. 5). In some implementations, the hollow tube is a narrow, hollow, cylinder with a length relatively short compared to the length of the catheter. In some implementations, the hollow tube is in the shape of a frustum. Because of the placement of the self-sealing filter (as recited in steps 606 and 608) and the hollow tube, when the sterilization gas flows through the hollow tube, the gas passes from a distal end of the sealed compartment through the filter to the elongate catheter, enabling fluid communication between the compartment and the catheter. However, the filter prevents liquid from passing through the hollow tube, while allowing gas to pass through the hollow tube, as described in relation to FIGS. 1-5 described above.

Though the steps of process 600 are recited in a specific order, the steps can be completed in any order.

Figure 7:
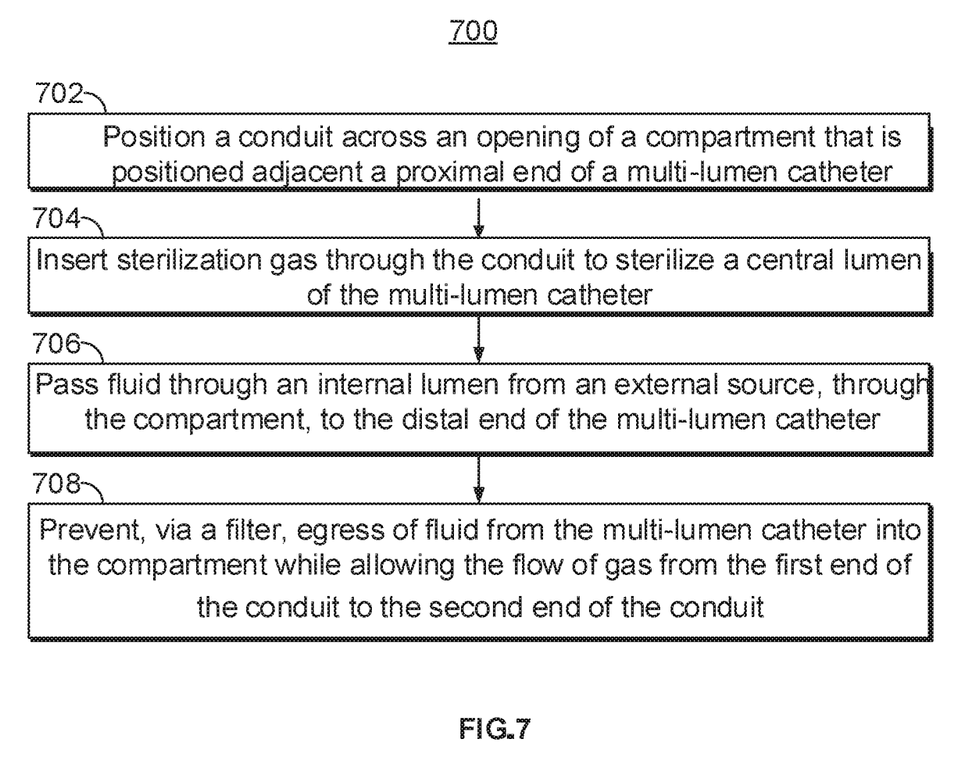
FIG. 7 shows a flowchart for preventing leaks from a catheter of an intravascular blood pump, according to certain implementations.

FIG. 7 shows a flowchart for preventing leaks from a catheter of an intracardiac blood pump, according to certain implementations. Process 700 starts at step 702, where a conduit is positioned across a first opening of a compartment. The compartment is positioned adjacent a proximal end of a multi-lumen catheter. In some implementations, the conduit extends from the interior of the compartment to a central lumen of the catheter. The conduit may have a proximal end and a distal end. For example, the compartment and the catheter may be connected with the conduit extending within and between the two, such that the proximal end of the conduit is within the compartment and the distal end of the conduit is within the catheter.

Process 700 continues to step 704, where sterilization gas is allowed to penetrate through the conduit. The sterilization gas sterilizes a central lumen of the multi-lumen catheter. In some implementations, the multi-lumen catheter is a main tube having a first diameter and defining the central lumen, with at least one secondary tube running through the length of the main tube within the central lumen, the secondary tube having a second diameter that is less than the first diameter. The sterilization gas may be fed through the conduit, such that it enters the central lumen (defined by the main tube) of the catheter. In some implementations, the pump is exposed to sterilization gas by being immersed in a gas-saturated environment. The gas can then penetrate through the proximal end of the conduit, which may be located within the compartment. The sterilization gas is thus delivered to the interior of the catheter to sterilize the central lumen.

Process 700 continues to step 706, where fluid is passed through a first lumen. The fluid may enter the first lumen from an external source. The first lumen extends through the compartment and to the distal end of the multi-lumen catheter. For example, fluid may be passed through the first lumen from an external source to the distal end of the multi-lumen catheter.

Process 700 continues to step 708, where the filter prevents egress of liquid from the multi-lumen catheter into the compartment, while allowing a flow of gas from the first end of the conduit to the second end of the conduit. For example, the filter may allow sterilization gas to reach the central lumen of the catheter but may prevent any liquid within the central lumen from reaching the compartment post sterilization.

Though the steps of process 700 are recited in a specific order, the steps can be completed in any order. In some implementations, gas penetration must occur prior to the filter coming in contact with liquid.

The foregoing is merely illustrative of the principles of the disclosure and the apparatuses can be practiced by other than the described aspects, which are presented for purposes of illustration and not of limitation. It is to be understood that the apparatuses disclosed herein, while shown for use in percutaneous insertion of blood pumps, may be applied to apparatuses in other applications requiring hemostasis.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions and alterations are ascertainable by one skilled in the art and could be made without departing from the scope of the information disclosed herein. All references cited herein are incorporated by reference in their entirety and made part of this application.

I claim:

1. An intracardiac blood pump system comprising:
a pump comprising a housing and a rotor disposed within the housing;
an elongate multi-lumen catheter having a proximal end, a distal end and a central lumen, wherein the distal end is adjacent the housing;
a compartment comprising a first opening and one or more side ports, the first opening of the compartment connected to the proximal end of the elongate multi-lumen catheter, the one or more side ports of the compartment located proximal of the first opening of the compartment;
at least one electronic element within the compartment;
a first lumen of the elongate multi-lumen catheter configured to carry liquid from an external source through the one or more side ports of the compartment and through the first opening of the compartment to the distal end of the elongate multi-lumen catheter;
a conduit extending through an interface between the compartment and the elongate multi-lumen catheter, the conduit comprising a first end located proximal of the first opening and a second end located distal of the first opening, the conduit configured to carry gas from the first end of the conduit through the first opening of the compartment to the second end of the conduit, the second end of the conduit being in fluid communication with the central lumen of the elongate multi-lumen catheter; and
a filter disposed within the conduit, wherein the filter is configured to prevent egress of the liquid from the elongate multi-lumen catheter into the compartment.

2. The intracardiac blood pump system of claim 1, wherein the filter is configured to allow flow of the gas from the first end of the conduit through the second end of the conduit and into the elongate multi-lumen catheter, while preventing egress of the liquid from the elongate multi-lumen catheter into the compartment.

3. The intracardiac blood pump system of claim 2, wherein the first lumen passes through the compartment and wherein the filter is configured to prevent a leak of liquid from the central lumen passing through the conduit and reaching the compartment.

4. The intracardiac blood pump system of claim 3, wherein the filter is located proximal of the first opening of the compartment.

5. The intracardiac blood pump system of claim 3, wherein the filter is located distal of the first opening of the compartment.

6. The intracardiac blood pump system of claim 3, wherein the filter extends across the first opening of the compartment.

7. The intracardiac blood pump system of claim 6, wherein a portion of the filter extends within the compartment.

8. The intracardiac blood pump system of claim 7, wherein the liquid comprises purge fluid and the purge fluid flows through the first lumen to the rotor to provide a barrier against blood ingress into the housing.

9. The intracardiac blood pump system of claim 1, wherein the liquid comprises at least one of: blood, saline, purge fluid, heparin and glucose.

10. The intracardiac blood pump system of claim 1, wherein the filter self-seals when exposed to liquid.

11. The intracardiac blood pump system of claim 10, wherein the filter is gas-permeable prior to liquid exposure.

12. The intracardiac blood pump system of claim 11, wherein the filter comprises a hydrogel adhered to pore walls of a porous substrate.

13. The intracardiac blood pump system of claim 12, wherein the porous substrate comprises at least one of: fibers, granules, or powder.

14. The intracardiac blood pump system of claim 1, wherein the at least one electronic element comprises at least one of: a circuit board, a wire, a soldered or surface mounted electrical connection, a resistor, a capacitor, an inductor, copper electrical connections, a memory, a pressure transducer, and a pressure sensor.

15. The intracardiac blood pump system of claim 1, wherein the gas carried by the conduit is sterilization gas.

16. The intracardiac blood pump system of claim 1, further comprising a connector at the first opening between the compartment and the elongate multi-lumen catheter, wherein the first lumen and the filter pass through the connector.

17. The intracardiac blood pump system of claim 16, wherein the connector has an inner volume and the filter fills at least 50 percent of the inner volume of the connector.

18. The intracardiac blood pump system of claim 1, wherein the filter is sized and shaped to fit within the conduit.

19. The intracardiac blood pump system of claim 18, wherein the filter is shaped as a frustum or a narrow cylinder.

20. The intracardiac blood pump system of claim 1, wherein the first lumen is within the central lumen.

* * * * *